United States Patent [19]

Urban et al.

[11] Patent Number: 5,037,658

[45] Date of Patent: Aug. 6, 1991

[54] DIRECT DRY COMPRESSIBLE ACETAMINOPHEN COMPOSITION

[75] Inventors: Joseph J. Urban, Richboro, Pa.; Richard R. Makowski, South Plainfield, N.J.

[73] Assignee: Hoechst-Roussel Pharmaceuticals, Inc., Somerville, N.J.

[21] Appl. No.: 407,047

[22] Filed: Sep. 14, 1989

[51] Int. Cl.$^5$ ............... A61K 31/05; A61K 9/26
[52] U.S. Cl. .................... 424/469; 424/465; 424/470; 424/486; 424/488; 514/960
[58] Field of Search ........... 424/458, 465, 488, 493; 514/166, 960

[56] References Cited

U.S. PATENT DOCUMENTS

| | | | |
|---|---|---|---|
| 3,773,922 | 11/1973 | Gergely et al. | 424/44 |
| 3,851,032 | 11/1974 | Andrews et al. | 264/109 |
| 3,859,431 | 1/1975 | Newton et al. | 424/37 |
| 3,873,694 | 3/1975 | Kanig | 424/127 |
| 3,923,974 | 12/1975 | Andrews et al. | 424/80 |
| 4,013,785 | 3/1977 | Weintraub et al. | 424/23 |
| 4,097,606 | 1/1988 | Chavkin et al. | 424/324 |
| 4,344,929 | 8/1982 | Bonsen et al. | 424/15 |
| 4,369,172 | 1/1983 | Schor et al. | 424/19 |
| 4,439,453 | 3/1984 | Vogel | 424/324 |
| 4,478,822 | 10/1984 | Haslam et al. | 424/78 |
| 4,515,802 | 5/1985 | Römer | 514/367 |
| 4,557,925 | 11/1985 | Lindahl et al. | 424/19 |
| 4,562,024 | 12/1985 | Rogerson | 264/117 |
| 4,600,479 | 7/1986 | Salpekar et al. | 424/80 |
| 4,606,909 | 8/1986 | Beckgard | 424/21 |
| 4,629,619 | 12/1986 | Lindahl et al. | 424/15 |
| 4,629,620 | 12/1986 | Lindahl et al. | 424/15 |
| 4,643,892 | 2/1987 | Peters et al. | 424/15 |
| 4,661,521 | 4/1987 | Salpekar et al. | 514/613 |
| 4,687,662 | 8/1987 | Schobel | 424/44 |
| 4,753,800 | 6/1988 | Mozda | 424/440 |
| 4,757,090 | 7/1988 | Salpekar et al. | 514/613 |
| 4,760,093 | 7/1988 | Blank et al. | 514/629 |
| 4,760,094 | 7/1988 | Blank et al. | 514/629 |
| 4,761,274 | 8/1988 | Denick, Jr. et al. | 424/48 |
| 4,767,789 | 8/1988 | Blank et al. | 514/629 |
| 4,771,077 | 9/1984 | Reuter et al. | 514/629 |
| 4,786,503 | 11/1988 | Edgren et al. | 424/443 |
| 4,820,522 | 4/1989 | Radebaugh et al. | 424/470 |

Primary Examiner—Thurman K. Page
Assistant Examiner—Edward J. Wilmann
Attorney, Agent, or Firm—Raymond R. Wittekind

[57] ABSTRACT

This invention relates to analgesic composition and more particularly, to a directly dry compressible composition comprising at least about 70% by dry weight of the composition of acetaminophen and a metal carboxymethyl starch present in an amount sufficient for it to function both as a binder and as a disintegrating agent.

12 Claims, No Drawings

DIRECT DRY COMPRESSIBLE ACETAMINOPHEN COMPOSITION

BACKGROUND OF THE INVENTION

1. Field of the Invention

This invention relates to an analgesic composition and more particularly to a directly dry compressible composition comprising at least about 70% by dry weight of the composition of acetaminophen and a metal carboxymethyl starch in an amount sufficient for it to function both as a binder and as a disintegrant.

2. Description of the Prior Art

Analgesic compositions comprising the active ingredient aspirin are easily tabletted using dry direct compression technologies. Such is not true with compositions having high concentrations of acetaminophen, e.g. in excess of 70 weight percent. Crystalline aspirin is easily tabletted since its crystals are soft and exhibit good plasticity/elasticity when compacted to tablets. Further, cohesive/adhesive bonding within the aspirin tablet is strong and the aspirin itself provides good lubricity to the formula. Accordingly, no lubricant is necessary in the formula used for aspirin tabletting. In contrast, acetaminophen crystals are hard and brittle and fracture very easily. The crystals have essentially no plasticity/elasticity and can be tabletted by the normal aspirin tabletting methods only by using relatively high levels of excipients, typically in excess of 30 weight percent. In addition, largely crystalline grade acetaminophen is sometimes employed to obtain acceptable tabletting, and these large crystals have the disadvantage of being slowly dissolved in the body and require additional tabletting aids to increase the rate of dissolution.

There is a substantial need in the art for a direct tabletting, free flowing, particulate acetaminophen composition which is capable of being directly dry compressed into a tablet having high hardness, short disintegration time and short dissolution time.

SUMMARY OF THE INVENTION

The present invention relates to an analgesic composition and more particularly, to a directly dry compressible composition comprising at least 70 percent by dry weight of the composition of acetaminophen.

The composition comprises an analgesic active ingredient of at least 70 percent by dry weight of the composition of acetaminophen and a metal carboxymethyl starch present in an amount sufficient for the starch to function both as a binder and as a disintegrating agent.

DETAILED DESCRIPTION

In accordance with the present invention, it has been found that the analgesic composition or formulation of the present invention, which comprises at least 70 percent by dry weight of the composition of acetaminophen and at least a metal carboxymethyl starch in an amount sufficient for the starch to act both as a binding agent, during the formulating stage of forming the composition and during the dry compression tabletting of the resultant composition, and as a disintegrating agent in the resultant tablet to impart desired characteristics to the tablet, provides a superior quality tablet with respect to hardness, friability, dissolution and disintegration.

Additional components of the formulation include other multifunctional materials, i.e. components present in sufficient amounts to enable each to perform a plurality of functions in either the formulation stage of the composition, e.g. as a binder, and/or during the direct dry compression stage of forming the tablet, e.g. as a lubricant, and/or imparting a desired characteristic to the resultant tablet, e.g. as a disintegrant. These multifunctional components are a pregelatinized starch and an ungelatinized starch. Additionally, a suitable additional or auxiliary binder, such as for example a polymer selected from a homopolymer and a copolymer of vinyl acetate, vinyl pyrrolidone and cellulose acetate, and any mixtures of the foregoing and a suitable auxiliary lubricant are present in the formulation.

A suitable acetaminophen is selected as the active ingredient of the analgesic composition or formulation. Preferably, the acetaminophen is provided in a finely divided form, i.e. of small particle size. Typically the acetaminophen will have at least seventy-five percent of its particles pass through a 100 mesh screen. The concentration of the acetaminophen will range from about 70 percent to about 94 percent by dry weight of the composition or formulation. An acceptable hardness of acetaminophen tablets ranges from 6 to 20 kp, preferably 7 to 12 kp, and if acetaminophen is present in an amount greater than about 94 percent by dry weight of the resultant composition, then the hardness of the tablet resulting therefrom goes below the acceptable hardness range.

Combined with the acetaminophen is a metal carboxymethyl starch which surprisingly acts both as a binder and as a disintegrating agent when combined with the acetaminophen, as well as other components which are contained in the formulation or composition. A metal carboxymethyl starch is any alkali metal salt of carboxymethyl starch. Preferably, a low substituted sodium carboxymethyl starch, i.e. a starch in which the degree with which the starch hydroxy groups are etherified with a sodium carboxymethyl group is low, is selected. A sodium carboxymethyl starch that is particularly suitable for the present invention is one in which the degree of substitution is about 0.20 to 0.35.

A commercially available sodium carboxymethyl starch that is suitable is marketed under the trade name PRIMOGEL. Others include PRIMOJEL L. V., the National Starch Company's sodium carboxymethyl starch No. 78-1702, EXPLOTAB®, sodium starch glycolate of the Mendell Company which is a low-substituted carboxymethyl ether of poly-alpha-glucopyranose obtained by the treatment of potato starch in the form of the sodium salt where about 25% of the glucose units are carboxymethylated, etc.

The metal carboxymethyl starch, e.g. sodium starch glycolate, is present in the composition or formulation in an amount sufficient for it to act as (1) a binder for all the ingredients of the composition both during the formulation of the composition, i.e. in forming the formulation or composition, and (2) as both a binder and disintegrant after the resultant formulation is compressed into a tablet. By compression is meant that the formulation is compacted into a tablet. The concentration of the metal carboxymethyl starch, e.g. sodium starch glycolate, ranges from about 1.7 percent to about 9.0 percent, preferably from about 2.5 percent to about 4.0 percent, most preferably from about 3.0 percent to aboute 3.4 percent by dry weight of the resultant composition. This starch is combined with the other components of the composition to be formulated in three separate steps, about one-third being added or combined initially in a dry state, thereafter about one-third being added or combined in the form of a paste and the remaining third being added or combined in a dry state. The paste typically comprises the starch, e.g. sodium starch glycolate, dispersed in a polar solvent, e.g. $H_2O$, ethanol, isopropyl alcohol, etc., in a concentration ranging from about 2 percent to about 15 percent by weight of the resultant paste.

The multifunctional ingredients of pregelatinized starch and ungelatinized starch are combined with the metal carboxymethyl starch in an amount sufficient for the pregelatinized and ungelatinized starches to act (a) as both a binder and disintegrant and (b) as a binder, a lubricant and disintegrant, respectively. The pregelatinized starch is starch (granules separated from the mature grain of corn or of wheat or from tubers of the potato) that has been chemically or mechanically processed to rupture all or a part of the granules in the presence of water and subsequently dried. The pregelatinized starch component can be obtained from any well known starch manufacturer such as, for example, the National Starch Corporation. Pregelatinized starches useful in the invention must meet all the NF.XV requirements for such starches. One suitable starch is National Starch Corporation's National 1551. Others include Colorcon's Starch 1500.

The pregelatinized starch is present in the composition or formulation in an amount sufficient for it to act (1) as a binder for the ingredients of the composition during both the formulation of the composition and after direct dry compression tabletting of the formulation and (2) as a disintegrant after the resultant formulation is directly dry compressed into a tablet. The concentration of the pregelatinized starch ranges from about 3.0 percent to about 6.0 percent, preferably from about 3.5 percent to about 4.8 percent, and most preferably from about 4.0 percent to about 4.3 percent by dry weight of the resultant composition.

Ungelatinized starch as compared to pregelatinized starch is untreated starch which exists in the form of discrete granules of complex structure which is derived from corn, potato, tapioca, sago, rice, etc., which granules have not been treated by heat or chemically e.g. with alkali. Suitable ungelatinized starches include natural, untreated corn starch, potato starch, etc. The low percentage gelatinized i.e. ungelatinized starch, e.g. zero percent gelatinized corn starch, is present in the resultant composition in a concentration in an amount sufficient for it to act as a lubricant during the direct dry compression tabletting of the resultant formulation, as a disintegrant when the tablet is formed and in an amount whereby it initially acts as a binder for the ingredients of the composition during the formulation of the composition. The concentration of the ungelatinized starch, e.g. corn starch, ranges from about 1.0 percent to about 10.0 percent, more preferably 1.5 to 3.0 percent and most preferred 2.0 to 2.5 percent by dry weight of the formulation.

Preferably present in the composition is a suitable auxiliary binder and a suitable auxiliary lubricant. Suitable auxiliary binders include hydroxypropylmethyl cellulose, corn starch, hydroxypropyl cellulose, gelatin, natural gums (e.g. gum acacia, gum tragacanth, etc.), sucrose, mannitol, ethyl cellulose. A preferred binder is a polymer selected from a homopolymer and a copolymer of vinyl acetate and vinyl pyrrolidone, e.g. polyvinylpyrrolidone (PVP), such as PVP® K-29-32.0, PVP® K26-28, PVP® K15-17, etc. A suitable auxiliary lubricant includes stearic acid, a metallic stearate (such as sodium, calcium, magnesium and zinc stearate, etc.), sodium lauryl sulfate, polyethylene glycol, hydrogenated vegetable oils, talc. A preferred lubricant is stearic acid.

The auxiliary binder is present in the composition in an amount ranging up to about 2.5 percent, preferrably from about 0.01 percent to about 2.5 percent and most preferably from about 0.01 percent to about 1.5 percent based on the dry weight of the resultant composition. The auxiliary lubricant is present in the composition in an amount up to about 2.5 percent, preferably from about 0.25 percent to about 2.5 percent, and most preferably from about 0.25 percent to about 0.75 percent by dry weight of the composition.

A filler such as lactose, microcrystalline cellulose, etc., well known in the art, may also be present to complete the composition.

The direct dry compression tabletting composition or formulation is typically prepared by first dry mixing the acetaminophen with about one-third of the total amount of the metal carboxymethyl starch, e.g. sodium starch glycolate, and preferably the pregelatinized starch and auxiliary binder, e.g. povidone, in a high shear pharmaceutical type mixer, such as a Zanchetta Roto-G, a Littleford MGT, a Baker-Perkins High Shear, a Littleford FKM mixer, etc.. It is preferred that such a high shear mixer (i.e. a mixer with a plow blade and a chopper blade), such as those described above, be employed. The dry blending is typically carried out at a temperature of 15° C. to 40° C. for 2 to 10 minutes to form a first, dry blended mixture.

A second portion, about one-third of the total metal carboxymethyl starch, e.g. sodium starch glycolate, is combined with a suitable solvent, e.g. $H_2O$, and is heated to a temperature of 70° C. to 95° C. for 2 to 15 minutes, whereby gelling occurs to form a paste in a concentration of about 2 to about 15 percent by total weight of starch. The paste is cooled typically to about 15° C. to 30° C. and is then combined with the first dry blended mixture and is again high shear mixed. This high shear mixing is again preferred to obtain a second mixture wherein the added components have been bound by the added metal carboxymethyl starch paste into discrete granules of material. Optionally, additional water may be added during this high shear granulation to complete the granulation. An addition of up to 40 percent by total weight of polar solvent, e.g. additional water, has been used to produce an acceptable granulation.

The resultant granulated mixture is dried in a conventional fluid bed dryer or a conventional oven, typically at a temperature of 45° C. to 75° C. for 20 to 40 minutes in a fluid bed dryer or for about 12 hours at a temperature of 40° C. to 50° C. in a conventional oven, to a typical moisture level of 0.9 to 2.3 percent by total weight. It has been found that with moisture levels of less than 0.8 percent by total weight that the resultant tablets have a tendency to cap and with a moisture level of more than 2.3 percent by total weight the resultant tablets exhibit lower hardness and compressibility ranges. The resultant dried material is milled, typically through a number 14, 16 or 18 mesh screen or equivalent screen using a conventional mill, whereby the resultant mixture has fines of not more than 20 percent of which pass through a 140 mesh screen. It has been found that with the increase in fines above 20 percent, that a decrease in the total range of compressibility of the resultant formulation occurs which is unacceptable because of lower tablet hardness and the tendency for the tablets to laminate.

The resultant milled mixture is combined in the dry state with the remaining amount of dry metal carboxymethyl starch (about one-third of the total), e.g. sodium starch glycolate, the ungelatinized starch, e.g. corn starch, and preferably the auxiliary lubricant, e.g. stearic acid, and dry mixed or blended in a conventional blender, typically at a temperature of 15° C. to 30° C. for 2 to 30 minutes to form the desired directly dry compressible tabletting composition or formulation.

The direct dry compressible tabletting composition is typically directly tabletted using a conventional tabletting apparatus, e.g. a Manesty Rotary Press, a Stokes Rotary Press, etc., at a temperature of 15° to 30° C. and a pressure of 0.4 to 1.2 tons. The resultant analgesic tablet of acetaminophen comprises bound granules. Each granule has (1) an inner or central core comprising acetaminophen, a portion of the metal carboxymethyl starch, e.g. sodium starch glycolate, which functions at least as a disintegrating agent, the pregelatinized starch and the auxiliary binder, e.g. povidone, and (2) an external layer or coat, continuous or discontinuous, covering at least a portion of the inner core, of an external disintegrant of at least a portion of the metal carboxymethyl starch and the ungelatinized starch, which leads to superior dissolution and disintegration of the finished tablet. It has also been found that the structure of the formulation is such that the resultant tablet hardness, within the acceptable 6 kp–20 kp range, has very little effect on dissolution, disintegration, friability or appearance.

The following examples and tables illustrate the invention. As used herein, the following terms have the meanings indicated:

(a) "Disintegration time" means the time measured using the disintegration-time test method set forth in U.S. Pharmacoepia (hereinafter "USP") XXI for uncoated tablets except that the disks are not employed;

(b) "Dissolution-time" means the time measured using the dissolution-time test method set forth in USP XXI for acetaminophen tablets;

(c) "Hardness" means the hardness measured on a Schleuniger Hardness Tester;

(d) "Friability" means the friability measured on a Erweka ® TA3 Friability Tester for 20 tablets after 130 revolutions.

Unless otherwise indicated, all tablet hardness values are averages for ten tablets and all tablet weights are averages obtained by weighing 10 tablets as a whole and dividing by 10. Further, unless otherwise indicated, tablet disintegration times were measured for tablets having about 7 kp hardness.

EXAMPLE 1

A directly dry tabletable granular composition was prepared in the following manner. 1800 g of acetaminophen (U.S.P.), 83 g pregelatinized starch, 21.4 g sodium starch glycolate and 0.2 g Povidone K 26-28 were blended together for 5 minutes at a speed of 750 rpm in a 5 liter Baker-Perkin high shear mixer. 21.4 g of sodium starch glycolate was dispersed in 360 g of purified water (U.S.P.), heated to 90° C., cooled to 25° C. and then added to the resultant acetaminophen containing mixture in the Baker-Perkin Mixer. The resultant mixture was granulated at a speed of 750 rpm with the chopper and plow of the mixer for 4.5 minutes. The resultant wet mass was dried in an Aeromatic fluid bed dryer, model STREA-1, to a moisture level (loss on drying) of 1.3 percent by total weight. The dried granules resulting were milled through a Frewitt Oscillator model GLA-OR2, equipped with a #18 screen. The milled granules were placed into a Paterson Kelly Blender and 44.3 g of corn starch (N.F.), 21.4 g sodium starch glycolate and 8.3 g of stearic acid were added. The resultant blend was mixed for 2.5 minutes and then discharged. The resultant granular or formulated composition was directly formed into tablets using a conventional tabletting apparatus. The resultant tablets had the properties shown in Table I below.

TABLE I

| | |
|---|---|
| Tablet Size (in.) | 13/32 (Flat Face |
| [F.F.B.E.] | Beveled Edge) |
| Total Weight (mg.) | 362 |
| Amount of Acetaminophen (mg.) | 325 |
| Disintegration Time (secs.) | 35 |
| Tablet Friability | 0.25% |
| (Roche Friabulator) [%] | 0.48 |

| Tablet Dissolution: Time (mins.) | % |
|---|---|
| 5 | 60.6 |
| 10 | 91.4 |
| 15 | 94.9 |
| 20 | 95.5 |
| 25 | 95.3 |
| 30 | 95.4 |
| hardness kp (S.C.) | 8(11) |

EXAMPLE 2

The procedure of Example 1 was repeated. The resultant tablets had the properties shown in Table II below.

TABLE II

| | |
|---|---|
| Tablet Size (in.) | 13/32 F.F.B.E. |
| Total Weight (mg.) | 362 |
| Amount of Acetaminophen (mg.) | 325 |
| Disintegration Time (secs.) | 21 |
| Tablet Friability | 0.30% |
| (Roche Friabulatory) [%] | 0.9 |

| Tablet Dissolution: Time (mins.) | % |
|---|---|
| 5 | 87.4 |
| 10 | 94.3 |
| 15 | 94.6 |
| 20 | 94.6 |
| 25 | 94.8 |
| 30 | 94.7 |
| hardness kp (S.C.) | 7(10) |

EXAMPLE 3

The procedure of Example 1 was repeated except for the following. 270.0 Kg of acetaminophen (U.S.P.), 12.45 Kg of pregelatinized starch, 3.21 Kg of sodium starch glycolate (N.F.) and 0.03 Kg of povidone were blended for 5 minutes in a Littleford LOD 105 mixer, chopper and plow being set at high speed. 3.21 Kg of sodium starch glycolate (N.F.) were dispersed in 54.0 Kg of purified water (U.S.P.) in a Groen Kettle and then mixed and heated to 90° C., cooled to 20° C. and was then added to the resultant mixture containing the acetaminophen in the Littleford mixer. The resultant mixture was granulated with the chopper and plow at high speed for 5½ minutes. The resultant wet mass was dried in an Aeromatic fluid bed dryer to a moisture level (loss on drying) of 1.7 percent by total weight. The resultant dry granules were milled through an oscillator #18 screen. The resultant milled granules were placed into a Paterson-Kelly Blender and 6.645 Kg of corn starch (N.F.), 3.21 Kg of sodium starch glycolate and 1.245 Kg of stearic acid was added thereto. The blend was mixed for 5 minutes and discharged. The granular composition was directly formed into tablets containing 325 and 500 mgs. of acetaminophen. The properties of the resultant tablets are shown in Table III below.

TABLE III

| Tablet Size (in.) | 7/16 Std. Concave | | | 13/32 F.F.B.E. | | |
|---|---|---|---|---|---|---|
| Weight of Acetaminophen (mgs.) | 500 | 500 | 500 | 325 | 325 | 325 |
| Total weight of Tablet (mgs.) | 556 | 556 | 556 | 362 | 362 | 362 |
| Disintegration Time (secs.) | 28 | 35 | 60 | 39 | 70 | 232 |
| Tablet Friability (%) | 0.6 | 0.5 | 0.5 | 0.5 | 0.3 | 0.3 |

| Dissolution Time | Percent (%) | | | Percent (%) | | |
|---|---|---|---|---|---|---|
| 5 | 79.1 | 69.1 | 51.9 | 48.4 | 51.0 | 10.4 |
| 10 | 97.0 | 96.4 | 92.5 | 92.8 | 83.2 | 66.2 |
| 15 | 98.2 | 98.3 | 99.4 | 97.2 | 95.7 | 82.3 |
| 20 | 98.4 | 98.4 | 99.9 | 97.8 | 98.0 | 91.5 |
| 25 | 98.6 | 98.6 | 100.0 | 97.6 | 98.2 | 95.2 |
| 30 | 98.6 | 98.6 | 99.9 | 97.8 | 98.0 | 96.4 |
| Hardness kp (S.C.) | 7(10) | 10(14) | 15(21) | 7(10) | 10(14) | 13(18) |

EXAMPLE 4

The tablets of Example 3 above were re-ground and were re-tabletted into tablets having 325 mg of acetaminophen. The properties of these reworked tablets are given below in Table IV.

TABLE IV

| Tablet Size (in.) | 13/32 F.F.B.E. |
|---|---|
| Amount of Acetaminophen (mg.) | 325 |
| Total Weight of Tablet (mg.) | 362 |
| Disintegrtion Time (secs.) | 40 |
| Tablet Friability [%] | 0.5 |

| Dissolution Time (mins.) | % |
|---|---|
| 5 | 38.7 |
| 10 | 88.7 |
| 15 | 98.5 |
| 20 | 99.1 |
| 25 | 99.3 |
| 30 | 99.2 |
| hardness kp (S.C.) | 7(10) |

EXAMPLE 5

27.0 Kg of acetaminophen (U.S.P.), 1.245 Kg of pregelatinized starch, 0.321 Kg of sodium starch glycolate (N.F.) and 0.003 Kg of povidone were blended for 5 minutes in a Littleford MGT mixer, chopper and plow being set at high speed. 0.321 Kg of sodium starch glycolate (N.F.) and 0.343 Kg of corn starch were dispersed in 5.400 Kg of purified water (U.S.P.) in a Groen Kettle and then mixed and heated to 90° C., cooled to 20° C. and added to the resultant mixture in the Littleford mixer. The mixture was granulated with chopper and plow at high speed for 5½ minutes. The resultant wet mass was dried in an aeromatic fluid bed dryer and a moisture level (loss on drying) of 1.9% percent by total weight. The resultant dry granules were milled through an oscillator #18 screen. The milled granules were placed into a Paterson-Kelly Blender and 0.321 Kg of corn starch (N.F.) 0.321 Kg of sodium starch glycolate and 0.125 Kg of stearic acid was added thereto. The blend was mixed for 3 minutes and discharged. The granular composition was directly formed into tablets containing 500 mg of acetaminophen. The properties of the resultant tablets are shown in Table V below:

TABLE V

| Tablet size (in.) | 7/16 Std. concave |
|---|---|
| Tablet weight (mg.) | 556 |
| Disintegration Time (Sec.) | 105 |
| Tablet Friability (%) | 0.45% |

| Dissolution (mins.) | % |
|---|---|
| 5 | 53.2 |
| 10 | 85.8 |
| 15 | 94.6 |
| 20 | 97.7 |
| 25 | 99.1 |
| 30 | 99.5 |
| Hardness KP (S.C.) | 12(26.8) |

It is to be understood that the above-described embodiments are simply illustrative of the principles of the invention. Various other modifications and changes may be made by those skilled in the art which will embody the principles of the invention and fall within the spirit and scope thereof.

We claim:
1. An analgesic composition comprising:
 (a) acetaminophen in an amount within the range from about 70 percent to about 94 percent by dry weight of the composition;
 (b) a metal carboxymethyl starch in an amount within the range from about 1.7 percent to about 9.0 percent by dry weight of the composition;
 (c) a pregelatinized starch in an amount within the range from about 3.0 percent to about 6.0 percent by dry weight of the composition; and
 (d) an ungelatinized starch in an amount within the range from about 1.0 percent to about 10.0 percent by dry weight of the composition, wherein the mixture comprising acetaminophen, pregelatinized starch, and metal carboxymethyl starch, prior to addition of ungelatinized starch, has a moisture content within the range of 0.8 percent to 2.3 percent of the dry weight of said mixture wherein said mixture has fines of not more than 20 percent of which pass through a 140-mest screen.

2. The composition of claim 1 wherein the metal carboxymethyl starch is sodium starch glycolate and the ungelatinized starch is corn starch.

3. The composition of claim 2 wherein acetaminophen is present in an amount of about 90 percent by dry weight of the composition, sodium starch glycolate is present in an amount of about 3.21 percent of the dry weight of the composition, the pregelatinized starch is present in an amount of about 4.15 percent by dry weight of the composition, and corn starch is present in an amount of about 2.215 percent by dry weight of the composition.

4. The composition of claim 1 which further comprises an auxiliary binder.

5. The composition of claim 4 wherein the auxiliary binder is selected from the group consisting of a homopolymer of vinyl acetate and vinyl pyrrolidone, a copolymer of vinyl acetate, vinyl pyrrolidone, cellulose acetate, mixtures of the foregoing.

6. The composition of claim 1 which further comprises an auxiliary lubricant.

7. An analgesic composition capable of being directly dry compressed into a tablet comprising:
 (a) acetaminophen in an amount within the range from about 70 percent to 94 percent by dry weight of the composition;
 (b) a metal carboxymethyl starch in an amount within the range from about 1.7 percent to about 9.0 percent by dry weight of the composition;
 (c) a pregelatinized starch in an amount within the range from about 3.0 percent to about 6.0 percent by dry weight of the composition; and
 (d) an ungelatinized starch in an amount within the range from about 1.0 percent to about 10.0 percent by dry weight of said mixture, and having a moisture content within the range of 0.8 percent to 2.3 percent of the dry weight of the composition, wherein the composition has fines of not more than 20 percent of which pass through a 140-mesh screen.

8. The composition of claim 7 wherein the metal carboxymethyl starch is sodium starch glycolate and the ungelatinized starch is corn starch.

9. The composition of claim 8 wherein acetaminophen is present in an amount of about 90 percent by dry weight of the composition, sodium starch glycolate is present in an amount of about 3.21 percent of the dry weight of the composition, the pregelatinized starch is present in an amount of about 4.15 percent by dry weight of the composition, and corn starch is present in an amount of about 2.215 percent by dry weight of the composition.

10. The composition of claim 7 which further comprises an auxiliary binder.

11. The composition of claim 10 wherein the auxiliary binder is selected from the group consisting of a homopolymer of vinyl acetate and vinyl pyrrolidone, a copolymer of vinyl acetate, vinyl pyrrolidone, cellulose acetate, and mixtures of the foregoing.

12. The composition of claim 7 which further comprises an auxiliary lubricant.

* * * * *